US008540650B2

(12) United States Patent
Salmi et al.

(10) Patent No.: US 8,540,650 B2
(45) Date of Patent: Sep. 24, 2013

(54) METHOD AND AN APPARATUS FOR MEASURING AND ANALYZING MOVEMENTS OF A HUMAN OR AN ANIMAL USING SOUND SIGNALS

(75) Inventors: Seppo Salmi, Helsinki (FI); Aino Salmi, Vantaa (FI); Väinö Virtanen, Vantaa (FI)

(73) Assignee: Smart Valley Software Oy, Vantaa (FI)

( * ) Notice: Subject to any disclaimer, the term of this patent is extended or adjusted under 35 U.S.C. 154(b) by 747 days.

(21) Appl. No.: 12/158,075

(22) PCT Filed: Dec. 19, 2006

(86) PCT No.: PCT/FI2006/000413
§ 371 (c)(1),
(2), (4) Date: Aug. 18, 2008

(87) PCT Pub. No.: WO2007/071812
PCT Pub. Date: Jun. 28, 2007

(65) Prior Publication Data
US 2009/0227888 A1     Sep. 10, 2009

(30) Foreign Application Priority Data

Dec. 20, 2005  (FI) ...................................... 20051300

(51) Int. Cl.
*A61B 5/11* (2006.01)
*A61B 5/08* (2006.01)
(52) U.S. Cl.
USPC ........................... 600/595; 600/586; 600/534
(58) Field of Classification Search
USPC ........................................................ 600/586
See application file for complete search history.

(56) References Cited

U.S. PATENT DOCUMENTS

| 2,499,483 | A | * | 3/1950 | Foy ................................ 446/219 |
| 4,428,454 | A | * | 1/1984 | Capaul et al. ................. 181/290 |
| 4,676,946 | A | * | 6/1987 | Feinzig et al. ................ 376/289 |
| 4,832,050 | A | * | 5/1989 | DiLullo ......................... 600/595 |
| 5,550,925 | A | * | 8/1996 | Hori et al. ........................ 381/98 |
| 5,749,365 | A | * | 5/1998 | Magill .......................... 600/484 |
| 5,797,852 | A | * | 8/1998 | Karakasoglu et al. ........ 600/529 |
| 5,961,447 | A |   | 10/1999 | Raviv et al. |
| 6,035,719 | A | * | 3/2000 | Toyota ............................ 73/649 |
| 6,063,043 | A | * | 5/2000 | Meyer et al. .................. 600/586 |
| 6,168,568 | B1 | * | 1/2001 | Gavriely ....................... 600/529 |

(Continued)

FOREIGN PATENT DOCUMENTS

DE       223 358 A1     6/1985
WO    WO 2005064476 A1 *  7/2005

OTHER PUBLICATIONS

Sony Portable MiniDisc Recorder user manual model MZ-N707.*

(Continued)

*Primary Examiner* — Sean Dougherty
*Assistant Examiner* — Michael C Stout
(74) *Attorney, Agent, or Firm* — Young & Thompson (57) ABSTRACT

A method, an arrangement and a computer application for conducting measurements of sleep disorders by capturing and analyzing the sounds associated with movements of the subject during a long-term or overnight monitoring session. A small-sized consumer apparatus such as an MP3 recorder may be attached to the subject for capturing the emanating sounds. Specially selected materials can be used to alter the spectral content of the sound so as to optimize the reception at the recording apparatus.

16 Claims, 4 Drawing Sheets

(56) References Cited

U.S. PATENT DOCUMENTS

| | | | |
|---|---|---|---|
| 6,887,208 B2* | 5/2005 | Kushnir et al. | 600/529 |
| 6,935,335 B1 | 8/2005 | Lehrman et al. | |
| 7,806,833 B2* | 10/2010 | Thiagarajan et al. | 600/528 |
| 7,861,821 B2* | 1/2011 | Connor | 181/141 |
| 2002/0072685 A1* | 6/2002 | Rymut et al. | 600/529 |
| 2003/0002685 A1* | 1/2003 | Werblud | 381/67 |
| 2003/0025604 A1* | 2/2003 | Freeman | 340/573.1 |
| 2003/0158466 A1* | 8/2003 | Lynn et al. | 600/300 |
| 2003/0208113 A1* | 11/2003 | Mault et al. | 600/316 |
| 2003/0226695 A1* | 12/2003 | Mault | 177/25.16 |
| 2003/0236474 A1* | 12/2003 | Singh | 600/595 |
| 2004/0056061 A1* | 3/2004 | Yang | 224/607 |
| 2004/0158193 A1* | 8/2004 | Bui et al. | 604/65 |
| 2004/0181115 A1* | 9/2004 | Sandyk et al. | 600/9 |
| 2004/0186390 A1* | 9/2004 | Ross et al. | 600/532 |
| 2005/0042416 A1* | 2/2005 | Blackmon et al. | 428/116 |
| 2005/0125256 A1* | 6/2005 | Schoenberg et al. | 705/2 |
| 2005/0159987 A1* | 7/2005 | Rosenfeld et al. | 705/3 |
| 2005/0187796 A1* | 8/2005 | Rosenfeld et al. | 705/3 |
| 2005/0271233 A1* | 12/2005 | Uchimura | 381/359 |
| 2006/0114809 A1* | 6/2006 | Hosokawa | 369/275.1 |
| 2006/0129067 A1* | 6/2006 | Grajales et al. | 600/586 |
| 2006/0153031 A1* | 7/2006 | Hirasawa | 369/47.13 |
| 2006/0155205 A1* | 7/2006 | Sotos et al. | 600/529 |
| 2006/0161459 A9* | 7/2006 | Rosenfeld et al. | 705/3 |
| 2006/0227991 A1* | 10/2006 | Klemme | 381/363 |

OTHER PUBLICATIONS

"The Overlooked Blanket—All Weather Sportsman's Blanket" Epinions 2012, hereinafter referred to as "Epinions".*

* cited by examiner

METHOD AND AN APPARATUS FOR MEASURING AND ANALYZING MOVEMENTS OF A HUMAN OR AN ANIMAL USING SOUND SIGNALS

FIELD OF THE INVENTION

The present invention relates to measuring and analyzing movements of human or animal limbs and/or tissues using the emanated sound signals as an analysis tool.

BACKGROUND

The movements of limbs, tissues and organs in medicine, physiological research, sleep research, ergonomics measurements for occupational physiology, etc may be measured using several methods. The most frequently used methods include strain, force and acceleration gauges, measurement of the electrical activity produced by the tissues (e.g. muscle electrical activity=electromyography=EMG) or measurement of changes in tissue movements or in properties of some materials affected by movements of the tissues (e.g. airflow caused by respiratory movements, changes in flow rate or temperature of the airflow). The measurement equipment is either fixed to the patient (e.g. strain gauge for changes in shape of the tissue) or he may be lying on a plate-shaped movement sensor ('sleep research mattress').

The measurements of movements caused by e.g. limbs or breathing (respiratory movements) are required in diagnostic studies and in the research of sleep disorders. Abnormal movement patterns (e.g. restless-legs syndrome, periodic movements of legs, see also the paragraph below) and pauses or lack of movements (e.g. pauses or irregularities of movements in otherwise regular breathing movements, i.e. apneas) are especially important for the diagnosis of sleep disorders. Concerning both adults and children, the number and distribution of movements are analyzed for the follow-ups of insomnia, poor/restless sleep, and daytime activity, for example.

One of the most common organic sleep disturbances is the 'restless legs-syndrome' (RLS) associated with repetitive periodic movements of legs and feet. Some patients know that they move their legs but other patients are not aware of it. If medical treatment is to be started the diagnosis of the disorder in question should be completed first. The diagnosis of the syndrome is determined utilizing a sleep recording called polysomnography. In this recording breathing and leg movements are typically studied using muscle electric activity pattern (EMG) with the measuring electrodes positioned on the legs (skin) during the sleep. The EMG signal is amplified and stored in the measurement equipment. The pauses in breathing, i.e. respiration, during sleep (~sleep apneas) are another important application of sleep recordings. The respiratory movements are followed by e.g. strain gauges in addition to the simultaneous measurement of amount and fluctuation of airflow using pressure and temperature sensors. The movements of the limbs may be followed also in the daytime using e.g. an acceleration sensor called actography, resembling a watch attached to the wrist of the subject. The distribution of movements is used to evaluate the periods when the subject was active or stationary/not moving and especially when he was laying and sleeping, which typically occurs during the night. The aforementioned phenomena should be measured with as little disturbance to the subject's sleep and sleeping position as possible. Maximally small and light measurement devices, sensors and systems are best suited to this task including the possible utilization in performing home recordings.

Disadvantageously the present recording devices have to be activated and partly fixed to the subject, e.g. a patient, by specially trained personnel in a hospital research unit using special straps, ergonomic tapes and glue-like paste. In some limited measurements the subject may take the devices and sensors home for the overnight study and return them immediately in the next morning to the hospital/unit where the measurement is completed by printing out the results from the devices. This laborious procedure always bears a risk of failure caused by some, even in principle somewhat minimal, external disturbances. Typically a plurality of measurement devices, in size of more than 10×10×2 cm, are required with even more than ten measurement sensors, in size of 1×1×1 cm, and the connecting electric wires. An electronic contact to the subject is frequently required setting additional requirements for the power supply and electronic safety. Therefore nowadays the measurements may often be possible only for a hospitalized patient sleeping in an "unfamiliar" environment, which also significantly increases the costs of the measurements.

The long duration of the recordings is an additional problem to overcome in achieving a successful result. One of the commonly used measurements (Sustained Immobility Test, SIT) takes one hour and all-night recordings with the subject lying on his bed take between 6 and 12 hours. The relatively long duration of the recordings makes all the aforesaid problems of the presently used methods even more complicated. The storage and analysis of the huge amount of signals and data from the long-term or overnight measurements is a demanding task. After completing the measurements and starting the required treatments, the effect of medication is determined using repeated measurements that are especially required in the long-term use and follow-up of treatments. The repeated measurements multiply the problems listed above.

One example of a prior art solution is disclosed in publication US2003/0236474 setting forth an arrangement for monitoring movements of a patient via various sensors in order to detect seizure conditions during periods of sleep, for example. A detector assembly comprising both a conditioning circuit for filtering/amplifying the input measurement signal from the sensing devices and a peak detectors circuit for low-pass filtering the signal and periodically detecting peaks therein is presented. The peak voltages are conveyed via an A/D converter into a microcontroller that then determinates the nature of the related movements on the basis thereof. The peak signals are, first of all, compared with threshold values in order to detect the patient's movement; the detected movements (e.g. seizure intervals) are recorded in a non-volatile memory for a period of time. The sensing devices may include among a number of options a sound detector that is optionally attached to a blanket, a quilt etc made of special material to amplify the movement-originated noise and thus ease the detection thereof.

Prior art solutions, in addition to the complexity of the arrangements, also commonly concentrate on the threshold-based analysis of the measurement signals as a result of which only detection pulses/periods comprising activity as determined by the threshold-criteria set are stored for further processing/analysis. Such approach requires using tailor-made, sophisticated, expensive, and well-calibrated (even case-specifically) measurement equipment to avoid conducting similarly awkward re-measurements due to bad calibration, for example.

Further, the diagnostics and treatment of sleep disorders is laborious, expensive and difficult. Some more practical measurement methods are being developed but all the present equipment in routine use costs several thousands of euros per piece.

The need for measurements is universal. The most common organic sleep disorders are snoring, breathing pauses during sleep (sleep apnea) and restless legs syndrome with periodic leg movements during sleep. The frequency of these disorders is between 5 and 10 percent of the adult population and even higher among the elderly. All patients with such disorders cannot be examined in the hospitals or research units, and a screening possibility is required too. The screening is performed exploiting the symptoms detected by the patient. The abnormalities during sleep are, however, quite difficult to recognize unless e.g. some other member of the patient's family has not detected the symptoms. The patients themselves may not be aware that they have a disorder with a potentially curable treatment. There fortunately still are several treatments available: treatment of sleep breathing problems like apneas with snoring operations, ventilation assisting devices and weight lose, treatment of insomnia with sleeping pills, and especially new drugs for restless legs syndrome. Nevertheless, for the restless legs syndrome there is a particularly great demand for new methods suitable for the diagnosis and follow-up of the effects of the treatment.

SUMMARY OF THE INVENTION

The objective of the current invention is to alleviate various aforementioned problems related to the utilization of prior art methods in conducting movement measurements.

The objective is achieved with a sound-based solution in which a contemporary or further cultivated electronic consumer apparatus capable of recording sound data such as a dictating machine, a sound/music (e.g. MP3) (player/)recorder, a mobile terminal, or a PDA (personal digital assistant) is utilized in conducting continuous audio recordings of movement-originated sounds of the subject. The recordings may be used in the study and research of the medical condition associated with the movements via utilization of a special analysis software. The analysis of the recorded audio signal may be based on both presence and lack of sounds therein as to be described hereinafter in more detail.

Accordingly, in one aspect of the current invention a portable, electronic consumer apparatus capable of sound recording is used in conducting sound-based measurements of sleep related physiological phenomena or abnormal phenomena related to sleep disorders, wherein said apparatus is positioned within a predetermined distance of a subject, said subject being a human or an animal, and configured to continuously record, over the measurement period, a digital sound signal obtained utilizing at least one microphone so as to capture sounds associated with the movements of the subject.

In this text a microphone is generally used to refer to a transducer that converts changes in air pressure into an electrical signal. In the context of the current invention the electric signal is further digitalized either directly in the microphone entity or by a subsequent component residing in the signal path.

As the aforesaid apparatus such as a digital dictating machine, a mobile terminal, a PDA, or a music (player/)recorder continuously records the ambient sounds with a predetermined or adaptive sampling rate (indeed, although the recording is made continuously, the sampling rate or other memory consumption-affecting parameters such as coding parameters may be adaptive based on the analysis of input sound; e.g. low amplitude periods may be stored with reduced resolution and bit-rate), the stored sound signal contains not only the periods of activity thus indicating the presence of (leg) movements, snoring, or breathing but also the periods without substantial activity (e.g. breathing pauses, ~apneas), which both are important for conducting a throughout analysis of the subject's situation. Preferably the apparatus stores the signal in a format that degrades the signal as little as possible, e.g. in a 'raw' (uncompressed) format or in a coded form (e.g. one of the MP3 formats, preferably >=32 kbit/s), possibly supporting a variable encoding rate. Only by having the whole recording also with substantially silent periods available, the scientific analysis following the measurements may be performed with increased accuracy. The analysis software then enables listening to the digitalized sound signal either from the beginning to the end or only at the desired positions (e.g. by point-and-click type function based on the signal visualization), optionally with increased playback speed for accelerating the analysis phase.

The invention also concerns a computer program for analyzing the audio signal obtained by the aforesaid measurement method, said program comprising code means adapted, when run on a computer, to execute the steps of:
  receiving and optionally decoding the audio signal,
  detecting the periods of movements or pauses, irregularities or lack of movements in regular movement patterns of the subject in the audio signal from the background activity according to preferably adaptive criteria,
  conducting statistical or mathematical analysis of the detected movements and/or pauses between the detected movements, said analysis comprising determination of a number of attributes including at least one attribute selected from the group consisting of: number, shape, amplitude, distribution, duration, and frequency of the detected movements and/or pauses, and
  rendering the signal, a part thereof, or at least one analysis result for visualization on a display to enable further analysis and visual investigation of the medical condition of the subject by trained personnel operating the computer.

The above analysis application is executed e.g. in a research unit that has agreed to study the situation of the subject. The research unit may be remote from the location wherein the measurements are conducted provided that the recorded data is transmitted either digitally, e.g. over a communications network, or via standard mail (e.g. a memory card enclosed in a preferably padded envelope) thereto.

According to another aspect of the current invention, a method for conducting sound-based measurements of sleep-related physiological phenomena or abnormal phenomena related to sleep disorders, wherein the subject of the measurements is either a human or an animal, is characterized in that it comprises:
  obtaining an equipment for conducting the measurement including an electronic consumer apparatus capable of digital sound recording,
  positioning the equipment including the apparatus at a measurement location so that at least one microphone thereof situates within a predetermined distance of a predetermined sound source relating to the subject so as to capture the sounds associated with the movements of the subject,
  initiating a continuous sound recording function at the apparatus,
  recording the sound signal as captured by said at least one microphone during a measurement period, terminating the recording function at the expiry of the measurement period, and sending the recorded sound signal to a remote entity.

In the above, the at least one microphone is either integrally formed with the apparatus or at least functionally (e.g. wirelessly) connected thereto.

The remote entity may refer to a PC (personal computer) of the subject wherefrom the data can be transmitted forward, or the remote entity may directly refer to a server in the responsible research unit, for example, if the apparatus itself includes the necessary communication means for such data transmission. In case the apparatus bears no actual communication means but only a removable memory stick/card, the memory stick/card comprising the recorded sound signal can be sent as such to the remote entity.

The measurement period has been preferably clearly informed to the subject beforehand so that the subject may himself control the apparatus to start and end measurements. Such control may be performed in real-time via control buttons on the housing of the apparatus, or by automated timing of the initiation and/or termination of the recording via a timer function (fixed or user-definable) provided by the software running in the apparatus. As a more high tech solution, the initiation/termination of the recording could be remotely controlled from the research unit provided that there is a communication path available between the apparatus and the research unit, which may be implemented over the Internet, for example.

In a further aspect of the current invention, a portable electronic arrangement for conducting sound-based measurements of sleep disorders, wherein the subject of the measurements is either a human or an animal, is characterized in that it comprises at least one microphone for capturing a sound signal, a processing unit for processing instructions, a memory for storing instructions and data, an attaching means for facilitating physical positioning to a predetermined measurement location such as a chest or a limb of the subject or a nearby object, and a user input means for receiving control information, wherein said arrangement is configured to initiate continuous, digital sound recording utilizing said at least one microphone in response to obtained control information so as to capture ambient sounds emanating from the vicinity of the measurement location during a measurement period and comprising sounds associated with the movements of the subject, configured to store at least part of the recorded sound data in said memory, and configured to stop the recording, upon termination of the measurement period, in response to an expiry of a timer or receipt of control information.

The arrangement may be further configured to transmit the recorded sound signal as such or in encoded form to a remote entity for forwarding and/or analysis.

In the above solution, said portable electronic arrangement may comprise a sound recording apparatus such as a dictating machine, a mobile terminal, a PDA, or a sound or music recorder such as an MP3 (player/)recorder. Either the apparatus housing includes said at least one microphone or the microphone is a separate one or at least separable from the apparatus and then preferably wirelessly connectable to the apparatus via e.g. Bluetooth, infrared, WLAN, or other feasible connection. The attaching means may refer to some special shaping, e.g. a hook, a clasp, an indent, a projection etc of the apparatus housing, which enables fastening of the apparatus/microphone directly to the predetermined measurement location or to a compatible counterpart on the measurement location. On the other hand, the attaching means may include a strap, tape, a stand/mount, an adhesive surface or an elastic band, which may be either fixed or at least removably connectable to the apparatus/microphone and the measurement location or a compatible counterpart positioned on the measurement location. Further, the attaching means may refer to specific clothing that includes means for positioning the apparatus and/or the microphone thereof close to the measurement location by means of a pocket, strap, a recess, etc.

The arrangement may further comprise a piece of specific, sound-modifying material as described hereinafter. The material may be provided as a separate entity (e.g. a sheet or a garment) to be positioned according to the instructions, or as integrated (e.g. a coating) or attachable to the recording apparatus itself or some other object, for example.

Optionally the arrangement is configured to transfer at least part of the sound data recorded and stored during the measurement period to a remote entity via a communication means of the recording device. The communication means may include a data interface compatible with USB (Universal Serial Bus), WLAN (Wireless Local Area Network), infrared communication, Bluetooth, or some other serial or parallel data transmission interface. However, as long as the device is ready-fitted with or at least supports in a form of a proper connector a removable memory stick/card, the memory stick/card may be provided with the sound data and then delivered forward as such.

The memory requirements for storing instructions and data differ from an embodiment to another. The memory may be internal/fixed and/or external/removable (e.g. a memory card or a stick) from the standpoint of the recording device. Further, the memory may consist of purely RAM type memory (random access, rewriteable) or a combination of ROM (read only) and RAM memories. First of all, the memory (both ROM and RAM) can be used to accommodate the software application that controls the functionalities of the device, and secondly, the memory may store the captured sound signal either in a raw (e.g. linear PCM) or further encoded form. The application may be downloadable/transferable from a remote server or device through the communication means. Alternatively, the application may be provided on a carrier medium such as a memory card. In case the recording device is in a substantially real-time fashion forwarding the sound data it receives and optionally encodes, only a smallish intermediate buffer is typically needed to ensure reliable data transmission to a remote entity, whereas if the recording device as such is supposed to store the whole recording covering e.g. six hours data, the memory size must be equally large. For example, six hours recording of mono 8-bit 20 kHz digital raw format sound consumes 6*60*60*20 kbytes of memory~roughly 430 Megabytes (in this exemplary calculation the byte length was 8 bits and one megabyte corresponded to $1000^2$ bytes). Compressing the captured sound by parameter representation or e.g. differential coding may lower the memory requirements, but respectively, processing capability requirements may shoot up and the sound quality decrease.

The user input means, if implemented using conventional means such as a number of buttons, a keypad, a touch screen, a touch pad, etc, is preferably positioned so that a risk of accidental activation is minimized, especially to prevent unintentional interruption of the recording phase after start-up (in scenarios where such interruption is possible or likely). This could cause the whole measurement to fail, if the subject fidgets around on his bed while sleeping, which activates 'stop recording' key. The subject probably realizes this not until the morning when he/she wakes up, and probably another full-scale measurement session is then needed as the undesired but unavoidable result. Placing the 'stop recording' functionality under a button or other touch-sensitive area that is positioned in an indent or recess, i.e. below the surrounding surface level of the device housing, can be used to prevent this setback, for example. Another solution is to use mechanical or software-based 'key lock' functions that require a certain sequence of keys or touch-sensitive areas to be depressed/touched optionally also within a predetermined time interval prior to activation of the keypad and the rest of the device for accepting other user-initiated commands. The different approaches for preventing the accidental activation/deactivation of functions in the device may be combined together.

Still in a further aspect of the current invention, an object comprising predetermined sound-modifying material is used in measuring sleep-related physiological phenomena or sleep disorders of a subject, said subject being a human or an animal and a microphone being utilized for capturing sounds associated with the movements of the subject, wherein said object comprising said predetermined material is positioned on a sound path so as to intentionally alter the spectral content of the sound according to a predetermined condition prior to receipt by the microphone.

One benefit of controlling the spectral content of the captured sound signal is that the properties/deficiencies of the recording apparatus (frequency range limitations, sensitivity limitations, disturbances) can be overcome by altering the spectral content of the sound so as to fall on the preferred range at the apparatus. Optionally even a plurality of objects may be used, e.g. a different one for each foot/subject, to enhance the separability between the sound sources (e.g. a limb or even a subject) in the recorded signal instead of or in addition to using multiple microphones or multiple recording devices, each having a microphone.

The expression "continuous recording" means in the digital context of the invention not necessarily absolutely continuous, i.e. analogue, but as limited by the utilized 'sampling rate' or 'sampling frequency', although the used transducer such as a microphone may indeed receive acoustic vibration continuously.

The terms "long-term" and "overnight" refer herein to a time period that extends over (>=) one hour or falls between 4-12 hours, respectively. Conducting an overnight recording does not necessarily require performing the measurements during the night-time, although that will probably give, in the described context of sleep disturbances, the most realistic results.

The term "predetermined distance" refers to a distance that is sufficient to capture the sound signal associated with the subject, i.e. breathing and/or movement sounds, with a decent separability from other sounds (e.g. background noise) possibly emanating in the same environment. Such sufficient distance is thus case-specific and determined by e.g. the sensitivity and directivity of the used microphone, body measurements of the subject, the location and nature of background noise sources in the measurement environment, and the desired signal-to-(background) noise ratio of the stored sound signal. The distance may differ e.g. between substantially immediate contact with the sound source (e.g. the recording apparatus is attached via a strap to the toe of the subject, so that the sound emanating from the contact between the toe and a sheet surface travels only a few millimeters or centimeters up to the capturing microphone) and tens of centimeters (the recording apparatus may be located in a selected central position like a chest for capturing sound from multiple sound sources such as the body and limbs contacts with external material, for example). Accordingly, the predetermined distance is not constant from a scenario to another as the sleeping position of one individual and various other parameters (weight and measurements of the subject, amplitude of respiratory and body movements, bed clothes and environment including background noises, nature and effect of facilities/furniture, etc) are not and cannot be kept constant either. This aspect makes absolute calibration and fixed detection levels of the prior art solutions disadvantageous. The adaptive calibration and statistically processed detection of movements and pauses, lack or irregularities in the movements using computer analysis of the whole signal is more reliable, which is the approach adopted in the current invention. The subject shall be anyhow provided with at least general instructions based on e.g. exemplary scenarios to position the microphone within a sufficient distance prior to conducting the measurement, i.e. within said predetermined distance.

The term "movement-originated" or "movement-indicating" refers herein to a sound that results from the movement of the subject; the movement causes contacts between at least two elements such as the moving element(s) and some surface or the medium in question. Thus the movements can be represented and analyzed via the resulting sounds. In this context the term "sound source" can thus either be seen as the particular part of the subject affecting the sound creation by contacting another entity/medium, or as the combination of that part and a contact element/medium. Also sounds directly or indirectly caused by breathing-related movement, e.g. respiratory movement, are considered as movement-originated sounds in the context of this invention.

The utility of the invention arises from a plurality of issues. First, the described solution is more economical and easier method e.g. for limited recordings such as screening of sleep disturbances compared to the previous methods in the routine use. While the typical prior art measurement equipment costs about 8000 euros and the single-use measurement sensors for every measurement cost between 10 to 20 euros, the price of a sound recorder such as an MP3-type music device or a dictation machine with recording facilities and a USB connection to a PC (personal computer), being thus suitable for use with the current invention, is often only between 30 to 300 euros.

The present invention can apply the most modern and highly developed properties of the devices aimed to the management of sound signals (including the high-capacity memory circuits, algorithms for data compression and storage, encoding algorithms, and low power consumption) in a novel manner. The contemporary rapid development of the aforesaid devices and equipment and the related new technical solutions further increase the utility of the invention.

In view of the foregoing the measurement devices according to the invention enable performing reliable long-term or overnight recording and storage of audio signals using the small, disposable or rechargeable batteries without external power supply, additional memory units or (electrically) connecting wires. The signal and related other data may be wirelessly (continuous or periodical transfer) transmitted during the measurement to the PC using e.g. BlueTooth, infrared (IR), or WLAN techniques. The PC may further forward the information to a service provider server (maintained by a medical clinic, for example) either continuously, in a timed manner, or in response to receiving a command by the user. Data in the memory of the measurement apparatus equipped with an USB or some other interface may be transmitted in some seconds only to the PC (or into a cell phone/PDA with compatible data transmission means) that then forwards the data, via available wireless or wired data transmission networks, for further detailed analysis at a remote location. It is also easy to bring/send the small memory stick/card with a price tag of few tens of euros and weight of few tens of grams back to the research institute in charge for analysis. The internal power source of the measurement device shall preferably last at least for the duration of the recording, i.e. one or more hours.

Reverting to the selection of suitable measurement equipment, the development of the microphones and recording devices in general has made the rapid development of new generation dictating machines possible. Accordingly, technical components required for conducting the measurements according to the invention are based on rapidly developing consumer electronics having good availability. In addition to fully specialized solutions, functionalities of a dictating machine may be included in a mobile terminal or a PDA, for example. A wireless microphone may transmit sound signals into this kind of device and/or directly from the device comprising/coupled with the microphone(s) to the PC. The devices are preferably using wireless data transfer methods like the ones listed above to transmit data from one device to another. Even small MP3 gadgets can be supplied with a recording/dictation function and a detachable, e.g. a battery driven, memory stick or a memory card with a weight of few ten grams and with a size of e.g. 10×1×1 cm or even less may digitally store more than ten hours of sound. This has been enabled by a decrease in the size of memory circuits and power consumption thereof and a leap in the algorithms related to signal compression. The "memory stick"-style or other budget sound recorders may be set e.g. in a continuous recording mode, while their cost is only some tens of euros. Various memory cards and sticks may be used in conjunction with mobile terminals and PDA's supporting a dictation option.

Secondly, while the prior art measurements of sleep disturbances were possible to perform solely in hospitals, research institutes and health centers with special skill and knowledge, the measurements applying the current invention may be performed without the presence of expert personnel and direct monitoring of the measurement. For example, a small battery driven measurement and/or a memory device like a microphone, a mobile terminal, a PDA, a dictation machine, or a combination thereof may be attached to the ankle or toe of a subject to store and/or transmit the sounds generated by the movements without disturbing the subject. The general-use dictation machines and functionally similar apparatuses are cheaper and simpler in construction and use compared with the tailor-made medical sleep recording devices. This makes it possible for the subject to perform the recording by himself locally instead of the hospital ward and expert personnel. The subject may be instructed to wear a sock or a shirt supplied with a fully featured recorder or a microphone connected thereto (wirelessly or by wire), and to press a 'start recording'-button in order to initiate the recording phase. The sounds induced by the movements are stored without causing any or at least major additional discomfort to the subject. The measurement is started and completed easily and economically, and preferably in as noiseless space as possible, in the subject's (patient's) home exploiting him also as the performer (initiator, supervisor etc) of the recording. Further measurements according to the present invention may be used to follow-up the effects of the started and on-going treatment in the constant and comfortable home environment; the effects of the possible drug or other treatments can be controlled in response to comparing the gathered measurement results to each other.

As movements in the context of the current invention almost unavoidably generate also sounds, they may be recorded and stored provided there is a sound-sensitive microphone attached near to or directly to the moving object. This effect can be concretized by reference to nowadays quite common situations wherein a powered-up cellular telephone resides in a user's pocket and accidentally takes a call without the user's intentional initiation. The clothes are then introducing rustling to the captured microphone signal that "synchronizes" to the walking. Even during sleep body movements cause sounds: rustling of bed clothing, sheets, blankets etc. Various textile or other materials generate different kind of rustling.

Similarly different surface materials of microphones have their specific effect on these noises and sounds that were considered in traditional measurements as erroneous noise signals (artifacts). If the microphone is attached to a properly selected clothing which may amplify and temporally and/or spectrally shape the sound signals associated and produced by the movements (like rustling or rattling special materials included in or connected to the aforementioned sock, trousers, shirt, vest, belt, or textiles like the ones under the sheet or bed cover of the sleeper, or such material included in/fixed to the microphone), the emanating sound signals may be amplified/spectrally shaped and therefore also stored more reliably. The spectral shaping may include transitions into a proper frequency band or widening/narrowing the band; if known that, for example, certain movements often cause (due to e.g. friction between normal clothing and normal bedding) relatively low-level and low-frequency sounds when captured, the used materials can be re-selected/new materials attached thereto so as to convert or additionally generate sounds that are easily recordable and analyzable by the recording gear and optional further analysis equipment. E.g. low frequency sounds (e.g. originally a continuous, sweeping-like sound) may be converted via the utilization of proper noise-inducing materials, e.g. irregular surfaces transforming a continuous movement into a non-continuous sound, to a higher frequency range, e.g. 300-3400 Hz employed in many contemporary systems adapted for speech storage/transfer. As a result, the sounds are not low-pass filtered prior to or during the A/D conversion in the digital recording apparatus that may have been initially designed for some other primary use.

Upon modifying the volume (intensity) and quality (e.g. spectral content) of movement-generated sound signals using textile or other materials with properties that accentuate and shift preferred frequencies, the recording and storage of the sound signals can be thus made more reliably. This is achieved by attaching the recording device like a microphone to a special piece of clothing (e.g. rustling or rattling special material or coating already present in a sock, trousers, shirt, belt, or in the bed textiles of the sleeping subject like in sheet or blanket), coated with an uneven plastic or metal coating, metal wire figures, rivets or some other objects to modify the sound signal when, for example, the legs of the subject are moving, during respiratory (breathing) movements, or when the subject is otherwise moving. Further, attachment of the recording device directly to the clothing is considered as a somewhat natural task from the viewpoint of the subject, because no additional bands, tapes or skin glues are required. As another example, movement of a foot or some other movement of a same kind may be separated better from the other night-time movements, or the movements and sounds generated by one person may be separated from the ones by another subject lying on the same or near-by bed (because both subjects are generating sounds and rustling) by pulling a special sock with a specially coated material over the foot of the first subject to be examined to modify the sounds. As an alternative, a microphone coated with special material for modifying the sounds may be attached to the foot. In that situation the sounds generated by the movements of the foot and the microphone attached to it are amplified and/or spectrally altered as desired. Instead of feet and socks, naturally also other materials/clothing may be utilized in relation to a preferred target location of the subject's body.

Yet, the analysis software developed as one aspect of the current invention performs the analysis of the measurement signal(s) and outputs (e.g. on a display, via a printer etc) the significant and interesting results required for e.g. medical analysis (follow-up, diagnosis, etc) that are typical for these kind of limited recordings of sleep disturbances, including the restless legs syndrome. The results are assessed as to their possible abnormality. Accordingly, appropriate measures such as starting a suitable treatment of the disorder can be taken. In particular, this kind of limited screening measurement facilitates detecting the abnormalities in early phases of the disorder, which is an important factor of successful treatment. The follow-up of the treatment may be performed with the measurement method described herein.

The analysis software of the invention analyzes the sound signals to detect separate movements, pauses between the movements, specific movement patterns, repeated movements etc. The typical parameters measured and calculated from the recordings with a limited number of signals are the number of the abnormal phenomena, the number of abnormalities divided by the duration of the recording and the duration of the abnormalities in time units like minutes. The medically most important and significant parameters are calculated and looked for to estimate the degree of the abnormality. The measurement results are visualized e.g. as graphs. These graphs are calibrated with normal median basic levels (e.g. in restless legs syndrome the level of the signal with no leg movements) to obtain a detection level for the movements. The absolute calibration of the movement-based sound signals is, in practice, impossible because the subject changes the sleeping position spontaneously; the statistically determined detection level is more adaptive to be used in long-term or overnight recordings. After the analysis of the detected movement this statistical basic level is used in a graphical output as the reference level. Thus the graphs visualize when the measured sound signals and movement signals exceed the measured normal basic level and further, how often such occasions are repeated etc. Additionally in the analysis of the results produced by the proposed arrangement various methods developed earlier for the analysis in the present field of scientific research may be utilized.

Further, the effects of therapies and treatments may be followed up using the aforementioned repeated measurements in the static home-environment of the subject and making control studies on the effect of the medical and other treatments by comparing the iterated measurement results. This is especially important to the medical companies in developing new drug therapies.

The measurement results and statistical analyses may be transmitted almost in real-time even in a global sense, optionally in a protected format, exploiting available data transmission networks to and between specialists and patients situated in different countries. The downloads, e.g. updates, of the analysis software of the invention may be likewise provided by local product representatives over data networks or even universally by a single representative only.

Equally, the charges such as a single user (=patient, ~subject) license fee for the legitimate use of the invention or payments from the service providers may be accounted universally (in protected format) through the networked money accounting systems (credit cards, Internet banking services etc).

Like the need for the measurements described, the industrial applicability of the invention is universal.

In an embodiment of the invention, the invention is used for conducting measurements relating to the study of restless legs syndrome, snoring and/or breathing pauses. Various add-on features including the utilization of special materials can be applied to cultivate the solution as described. Further alternative approaches are likewise presented.

BRIEF DESCRIPTION OF THE ATTACHED DRAWINGS

In the following, embodiments of the invention are described with reference to the drawings in which.

DETAILED DESCRIPTION OF THE EMBODIMENTS

Figure 1:
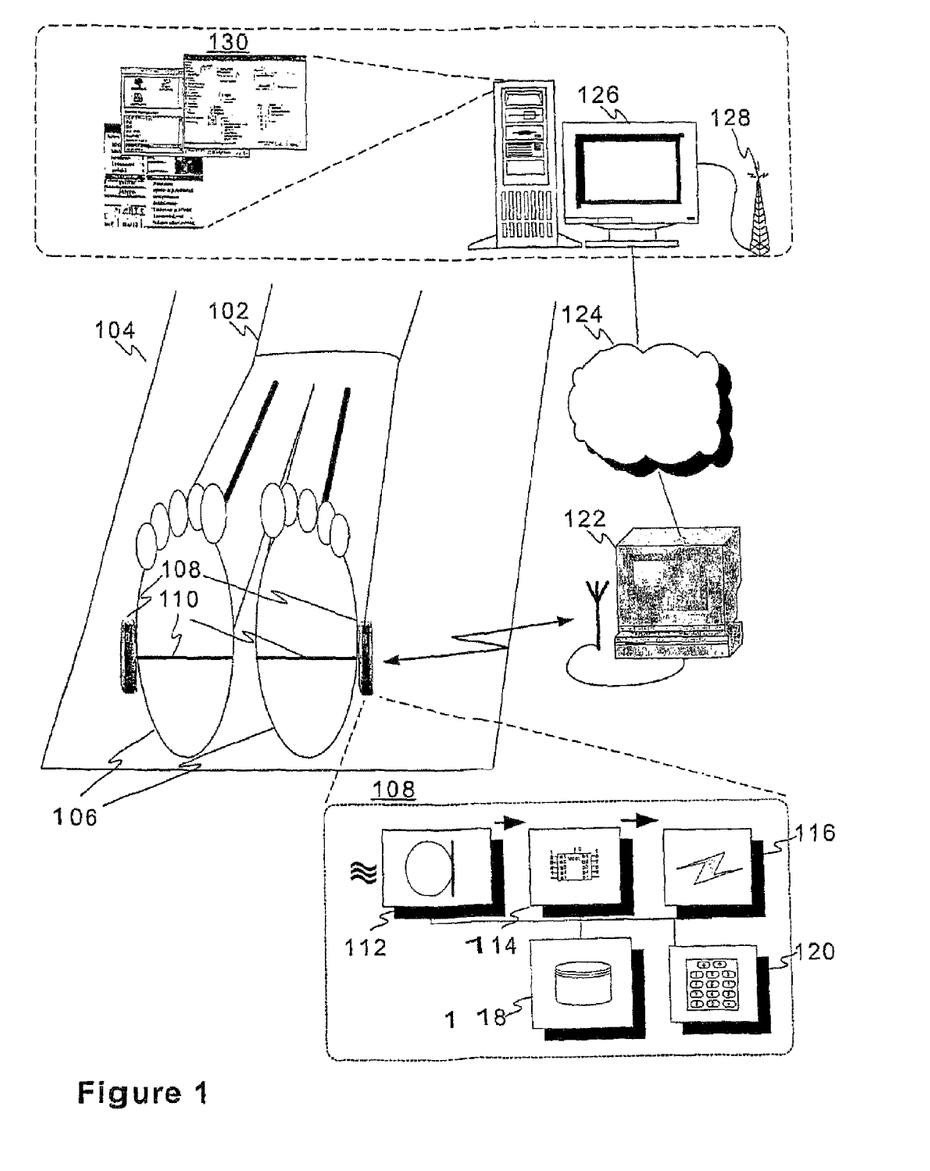
FIG. 1 schematically represents a system in accordance with one embodiment of the present invention.

FIG. 1 discloses a system according to an embodiment of the invention comprising a number of electronic sound recording devices equipped with internal or external (wired/wireless) microphone(s). The subject 102 is lying on his bed 104 and one or more small-sized devices 108 capable of sound recording such as dictation devices or music (MP3, WMA, WAV etc) players with recording function, or at least microphones communicating preferably wirelessly therewith, are coupled to the feet 106 of the subject 102 via straps 110. An exemplary block diagram of devices' 108 internals is shown in a separate zoom-in block, wherein element 112 depicts a microphone or a comparable sound converting entity (~transducer) that may also comprise an integrated A/D converter that outputs the captured audio signal e.g. in 8-48 kHz, 8-24 bit digital form, for example. The microphone 112 may be an external or a removable one in which case it may be positioned with some distance from the rest of the device 108 provided that it contains a wireless transmitter to send the captured sound to the device 108. Further, the device 108 may comprise a plurality of microphones 112, one or some of which may further be removable and support remote positioning as explained above. In case of multiple microphones 112, also multiple sound signals are captured for storage and forwarding thus setting higher requirements for necessary memory and/or data transfer capacity. Alternatively, the signals from multiple microphones may be combined to a single signal to gain memory/data transfer capacity savings; simultaneously, however, the spatiality aspect provided by the spatially separated microphones, e.g. a microphone array, is lost in the analysis phase, and source based classification of sounds may suffer. Combining may tale place at the device 108, PC 122, or server 126, i.e. anywhere on the transmission path prior to or at the final storage/analysis location.

The device 108 further includes a processing unit 114, e.g. a microprocessor, a microcontroller, a programmable logic array, a DSP, or a plurality of those connected together. The processing unit 114 takes care of controlling the device functionalities based on instructions included in an application stored in a memory 118 of one or more memory chips or cards. Element 116 depicts various communication means the device 108 has for I/O purposes such as a wireless transceiver (WLAN, infrared, Bluetooth, etc) or a (wired) network interface, e.g. an Ethernet adapter. Communication means 116 is not a compulsory element provided that the memory 118 comprises a removable memory stick or card that can be connected to another apparatus comprising the data transfer capability over the available communications network. Alternatively, a removable memory stick/card may be sent via a traditional post to the research unit in charge, which however delays the overall procedure extending from conducting the measurements to obtaining the analysis results.

Further, the device 108 includes a user input means 120 for obtaining control information in a form of buttons, a touch screen, a touch pad, a keypad, etc. Optionally, the device 108 may support speech recognition based control as enabled by the presence of the microphone 112 and optional voice recognition software stored in the memory 118 and running on the processing unit 114. Further optionally, the device 108 may include a display for visualizing the captured sound signal or parameters calculated therefrom.

Via the communication means 116 the device 108 can forward the captured and digitalized audio signal to the nearby PC 122 or other electronic communication apparatus providing access to the research unit in charge over an applicable communications network 124 such as the Internet or a cellular network like GSM, CDMA, and UMTS networks with data transfer support. The measurement data may be transmitted in a single message or split into a plurality of smaller messages, if desired.

The research unit, which may thus have a data connection both to wired 124 and wireless networks 128, comprises the necessary hardware, e.g. a server 126, and tailor-made software 130 for performing medical analysis under the control of trained professionals and on the basis of the received measurement data.

In certain cases the above division between sound recording devices and data transmission devices may be rather fickle as even the recording device as such may bear the storage and transmission capability (or even analysis capability) to first store and then send the measurement data directly to the research unit. In that cases the device 108 such as a sophisticated mobile terminal or a PDA may be considered to embed the features of devices 108 and 122 as visualized. On the other hand, other elements than depicted in the figure can be additionally utilized; for example, in the scenario of wireless microphones, the microphones that are coupled to the subject's feet may be configured to (if containing an A/D converter, with modest buffering though) forward the captured audio signal substantially in real-time fashion to the device 108, device 122 or a combination thereof for storage and forwarding. Forwarding data to the research unit takes then place automatically (timed or right after finishing the measurement) or due to user initiation. It is also feasible to forward the available measurement data to the research unit while the measurement is still ongoing so that the trained personnel may start analysis without a delay.

In the restless legs syndrome repeated periodic movements of the subject's legs disturb his sleep. Some persons are conscious that they tend to move their legs whereas some others do not realize that. If the syndrome is ought to be treated by the appropriate medical treatment, the accuracy of preliminary and intermediate analyses and ultimately the final diagnosis should be ascertained. Likewise, in case of pauses or lack of movements (e.g. pauses in breathing movements, called apneas) the analysis method should be as reliable as possible starting from the recording of the raw data signal comprising movement-originated sounds and pauses between. The method of the invention provides a feasible basis for studying both the restless legs syndrome and breathing pauses, for example.

Figure 2:
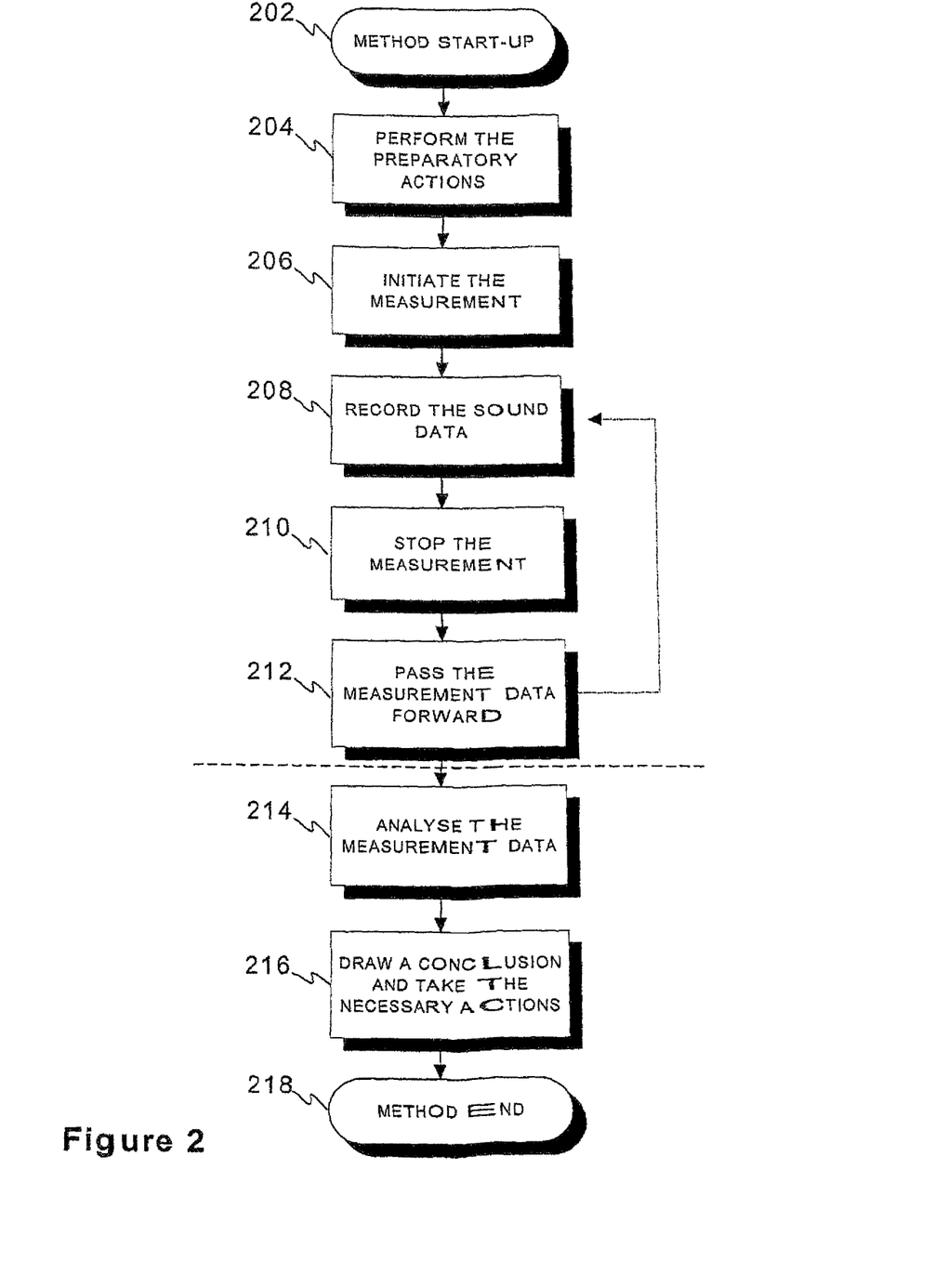
FIG. 2 discloses a flow diagram of one embodiment according to the method of the invention.

FIG. 2 discloses a flow diagram according to an embodiment of the invention. The core of the invention can be used for measuring and analyzing the movements in a plurality of slightly varying contexts, which is further highlighted with reference to FIGS. 3A and 3B.

The study is typically of a long-term or overnight nature and the execution starts from an initial phase 202 defining the method start-up including providing the subject with necessary equipment and instructions by the unit/institute responsible for the study. As the sound signals representing the sounds generated by the movements are to be recorded and stored for subsequent analysis, the applicable gear may include, e.g. in the context of restless legs measurements, a pair of electronic recorders such as dictation machines, each comprising a microphone and support for digital recording. In the case of measuring breathing pauses using only one device/microphone is equally applicable.

These devices may include an internal memory chip, a memory card, and/or a digital memory stick and an USB connector providing a reasonably small-sized, fast and reliable data interface that is compatible with a PC or other preferred destination device used for transferring measurement signal to the target server at the institute or other "service provider" premises in more vernacular language. Memory capacity of at least 128-256 MB and an internal, preferably rechargeable and/or replaceable battery, which allows a continuous all-night recording without external power cord, are preferred depending on the used sound encoding technology, if any. The device is advantageously small-sized, e.g. of matchbox size, to avoid physically disturbing the subject: accordingly, an exemplary weight of a suitable device is without batteries about 20 grams. The user may already own at least part of the gear (e.g. a mobile terminal or an MP3 player/dictation machine) required for conducting the measurements, in which case he is provided with the remaining equipment (e.g. straps, clothing, memory card, software etc) for duly performing the task.

In addition to the recorders, the following items may be delivered to the subjects for the study of the restless legs syndrome:

straps or other attaching means for attaching the device(s) to the legs (or body/limbs, measurement location in general), and information required to complete the study (electronic, paper, verbal delivery).

Respectively, items useful in conducting the breathing pauses analysis encompass:

one special type of clothing like a two-layer vest with means to attach the recording device(s)/microphone(s) thereto, and information required for completing the study (electronic, paper, verbal delivery).

Next the subject properly situates the devices and performs other preparatory actions 204 such as switching the electronic devices into a proper functional mode etc, whereby for monitoring restless legs he may especially take the actions to attach the aforementioned devices into his left foot and right foot using the attaching straps whereas for breathing pauses analysis e.g. the vest carrying the recording device shall be dressed up; the subject will be thus wearing a special piece of cloth around his chest, e.g. the two-layer vest configured to elastically adapt to the breathing movements (respiratory movements) of the subject. The inner layer of the vest may be made tighter and more elastic than the outer layer, therefore allowing the inner layer to move or stretch more than the outer layer when the subject is breathing. In addition the outer surface of the inner layer and the inner surface of the outer layer are specially coated to be uneven or rough. This affects (amplify and/or spectrally shape/shift) the sounds of the movements of the chest to be studied when the rough outer and inner surfaces are moving against each other and generating rustles. The recording device is attached onto the chest of the subject, e.g. into a pocket of the specially build shirt of a special material, using an attaching loop, strap or other attaching tool in order to record the sound signals.

The measurement begins 206 during which the sounds are generally captured, transformed into representative electronic signals and optionally further processed prior to storage 208. The subject may start the measurement by himself by pressing the 'start recording' push button of the device(s) when going to sleep. The associated devices will record the sounds generated by the movements of e.g. feet, other limbs, or chest during the night or a corresponding period either via external or internal microphones thereof.

Positioning the microphones or the devices carrying the microphones properly certainly has an effect in the outcome; the microphones are advantageously situated in the vicinity of the sound sources to be tracked, which is likewise advantageously far from other potential sound sources. In home environment the other sound sources may include e.g. loud clocks, pets, street and traffic noise emanating through the near-by window, etc.

One of the devices (microphone unit, storage unit, and forwarding unit, if not at least partly integrated together) may be configured to process the captured audio signal applying signal-processing means available in software and/or hardware of the device. For example, a noise reduction algorithm/module may be utilized to attenuate the pseudo-stationary noise possibly present in the background while conducting the measurements. Such algorithms may gradually adapt to the background noise characteristics and then delete the synthesized noise estimate from the captured audio signal prior to storing/forwarding the audio signal to the next element of the transmission chain. Such noise tracking typically takes place either in temporal domain (e.g. adaptive LMS-filter-based solutions) or frequency domain (e.g. spectral subtraction techniques). Simultaneous use of a plurality of microphones during the measurement phase may improve the noise reduction performance as the noise signal can be estimated with increased resolution based on the possible spatial separation between the background noise and other sounds. Further, spectral shaping technology may be applied to emphasize preferred frequencies and/or de-emphasize the rest. For example, if the characteristics of the sounds generated by the movement to be tracked is known e.g. due to the specific materials used, related frequencies may be favored over the remaining frequencies in the signal.

Although a so-called raw format wherein the captured audio signal is stored as independent samples with a predetermined, fixed resolution defined by both the bits-per-sample criterion and the utilized sample rate is the most straightforward solution for data storage due to generally maximum data preservation therein, alternative formats may be applied in situations wherein e.g. the storage space is limited or some other data format gives an improved temporal or frequency resolution on the desired characteristics of the captured signal. Parametric representations starting from logarithmic (u/a-law CCITT G.711 etc) PCM and ending in sophisticated but typically also more or less lossy compression algorithms (MPEG (e.g. 'MP3' or AAC), LP/CELP-codecs (Code Excited Linear Prediction), ADPCM (adaptive differential PCM), RealAudio, etc) may achieve compression ratios up to 15:1 or even more without distorting the sound characteristics too much for the subsequent analysis. Instead of time-sample representation, a period of the captured sound signal may be represented through various filter coefficients, gain parameters, and excitation signals.

In the morning/after the measurement period the subject stops 210 the recording function by pressing, for example, the 'stop recording' push button and loosens the attaching straps or takes off the special clothing like the vest. Alternatively the recording functionality may be timed (e.g. user-programmed) and the recording status thus automatically terminates in expiry of a timer.

The subject delivers 212 either via postal services or physical visit the devices or at least the memory storage units carrying the stored sound signals to the institute responsible for the study. Alternatively, the subject may transmit the data from the memory storage device first to his home PC and further using available data transmission connections (like the Internet) to the institute responsible for the study. Such data transmission may also be automated, e.g. user-definable or inherent in the used applications of the recording and/or intermediate devices. As a further alternative or supplementary feature, the recording device(s) may include at least limited processing, analysis, and visualization application for immediate local analysis. In case the recording device itself (e.g. a mobile terminal) comprises data transfer means, use of an intermediate PC is naturally not mandatory. The order of phases 210 and 212 may be reversed in a case wherein the recording device substantially in real-time transmits the captured and optionally encoded sound data forward while still recording new data, whereby the execution of phases 208 and 212 is alternatingly continued in a loop until the end of the measurement period presented by phase 210.

The dotted line in the figure depicts the optional location change from the measurement environment (e.g. home of the subject) to the analysis environment (research lab etc) that likely takes place between phases 212 and 214.

The institute responsible for the study may perform the transfer of the received sound signals further to a special analysis device for proper data analysis using e.g. the USB connection of the received memory storage units and the USB connection line of the analysis computer.

The analysis device, e.g. a computer device equipped with analysis software, is used in the institute responsible for the study to perform specific computerized processing to analyse 214 the sounds in the recorded signals. The software is generating statistical and mathematical parameters, values, indices etc as analysis results in order to facilitate the trained personnel in estimating the situation and ultimately making the diagnosis and follow-up of different disorders or diseases the subject possibly has. Intermediate or final conclusion phase (e.g. indicating need for further study, giving instructions to the subject etc) resulting from the analysis is shown as box 216 in the figure.

Using the aforementioned process the subject may also undertake repeated measurements. Accordingly, the follow-up of the effects of possible treatments is possible in constant home environment thus allowing control of the medical and other treatments by comparing the results of the iterated measurements to each other.

The method execution is ended in step 218; it was already made clear earlier that the selected preceding method steps may be re-executed either consecutively or in parallel in case the data acquisition, forwarding, and analysis take place at least partially simultaneously, or in the case of re-measurements/follow-up.

Figure 3A:
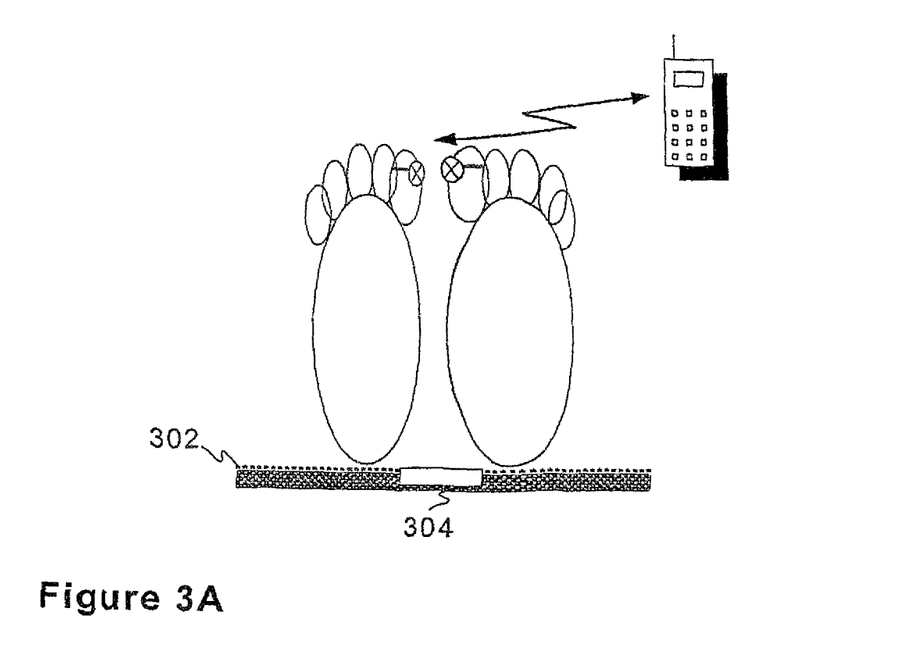
FIG. 3A visualizes the applicability of the aforementioned system and relating method as further supplemented by the use of predetermined, sound-modifying materials.

FIG. 3A depicts the exploitation of a predetermined material used for shaping the amplitude and/or frequency response of sounds caused by the body movements.

In this aspect of the invention the sound signals produced by the movements are amplified using the supporting method and product of the invention: e.g. a special object such as a sheet 302 made of predetermined material shaping the sounds generated by the movements to be studied can be used, in which case the sheet is located under the feet of the subject, for example. The surface of the sheet may be uneven, multilayered, and/or rough to induce rustling or rattling sounds or made of special material containing e.g. metal wires to induce rattling sounds when touched by the feet. Likewise, hollow pearls of hard plastics causing jingling sounds as well as elastic materials and folio sheets causing sounds that can be described as "creaking" or "squeaking" when stretched, are applicable. The used objects and material thereof are preferably passive, i.e. the sound shaping occurs due to their physical properties. Alternatively or additionally, active means such as an electric sound-modifying apparatus that captures sounds and modifies their properties prior to outputting them (e.g. via a loudspeaker) could be used; nevertheless, such active means requires a power source of its own, which can be left out from the passive solutions.

Prior to the measurements the subject puts the sheet on the bed beneath his feet and places the recording device or at least a wireless microphone thereof near the bed. The recorder may in this case be e.g. a mobile terminal that is functionally connected using Bluetooth or other available connectivity means to a pair of wireless microphones attached to the subject's halluces, one per hallux. Then the microphones will capture and forward the sounds produced by the legs while the sheet manufactured from the special material amplifies and/or spectrally shifts/modifies the sounds before capture. After finishing the measurements the subject delivers the rental equipment including the special sheet and/or the memory storage device (e.g. memory card of the mobile terminal) back to the institute responsible for the study.

Correspondingly, specific materials can be used in coating the equipment of the method. E.g. a microphone or the device comprising the microphone (dictation machine, mobile terminal, sound recorder etc) can be coated with a material generating rustling or other type of noises. When the clothing worn during the measurements consisted of several layers, it could consist of two or more separate parts and of different materials. The different parts could react differently to the movements and rub each other in a distinctive manner to generate the sound signals enhancing the movement to be studied. In theses applications the microphone and the associated storage device can be located between the inner and outer surface or between some of the several layers of the specially constructed clothing like a vest. This may enhance the sound amplification and/or shaping properties of the selected materials and dampen the effect of disturbing background noises.

Within the scope of the invention it is possible as mentioned herein earlier to record sound signals from a plurality of sound sources simultaneously and independently using a desired number of microphones. E.g. in restless legs syndrome it is in most cases sufficient to summate the activity of the both legs for adequate analysis. It may even be reasonable to utilize only a single microphone attached e.g. to one foot of the subject to record the sound signals produced by the both legs and/or feet. As a further alternative, there may be only one microphone (or a device comprising the microphone) that is placed in a pocket 304 of the sheet under the legs in which case the microphone can simultaneously record the sound signals produced by both legs and feet.

Figure 3B:
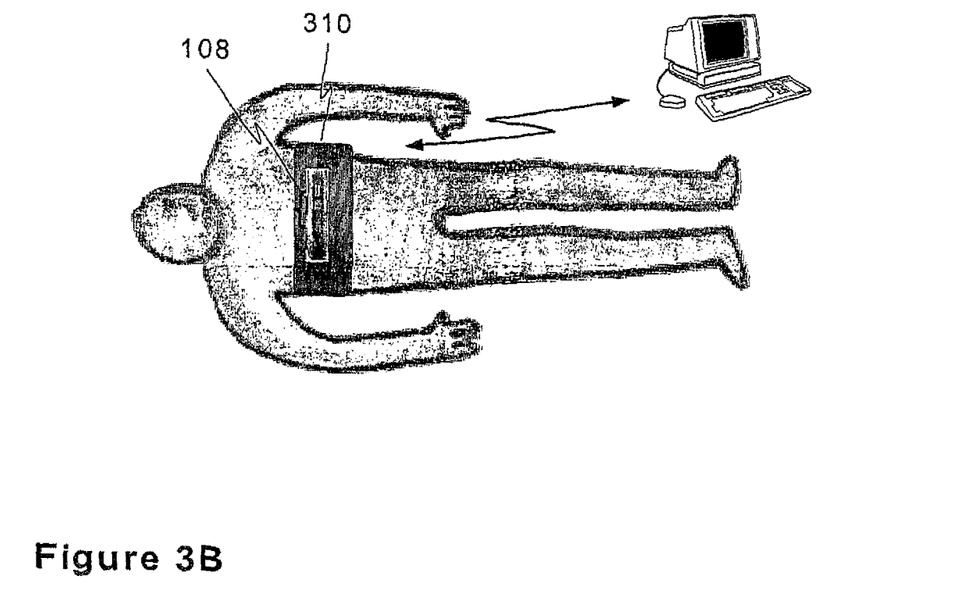
FIG. 3B visualizes the applicability of the aforementioned system and relating method especially in the exemplary context of breathing pauses measurements.

FIG. 3B illustrates a vest 310 the subject may wear during the study of sleep apneas. The vest 310 comprises a number of layers that preferably elastically adapt to the respiratory movements of the subject as explained hereinbefore. The recording device 108 or at least the microphone(s) preferably wirelessly connected thereto is attached to the vest by strap(s), clip(s), etc, or inserted to a pocket thereof. Alternatively, the device 108 may be situated near the vest 310 without a direct contact thereto, if the shape/size of the device 108 or structure of the vest 310 does not support convenient mechanical coupling between them.

As a further example of the applicability of the invention is to use the equipment of the invention to record and measure snoring sounds, a routine measurement in sleep recordings, which could be cleverly incorporated into the arrangement of the invention. For example, a (second) identical device could be located nearer to the mouth of the subject and thus perform focused recording of the snoring sounds during the night. The stored signals can be analyzed with the analysis device and software developed especially to this application, or with the help of some traditional analysis methods available.

Measuring both the snoring sounds and movement-indicating sounds provides also synergy effects. For example, leg movements occurring after apnea or intermittent snoring typically indicates that the subject has awoken to enable normal, smooth breathing again. Such awakenings break the structure of sleep, which is an important aspect in the analysis of sleep disorders.

Specially in the follow-up and long-term/overnight monitoring the measurement and/or analysis software, the results obtained and the general possibility to use the invention could be applied by the subject himself on his home PC and using the public data transmission networks such as the Internet. Exploiting modern telemedicine would thus offer a new service level and accuracy independent on the distance between the research unit and the subject. The current solution even enables studying newborns or small children in their homes.

Figure 4:
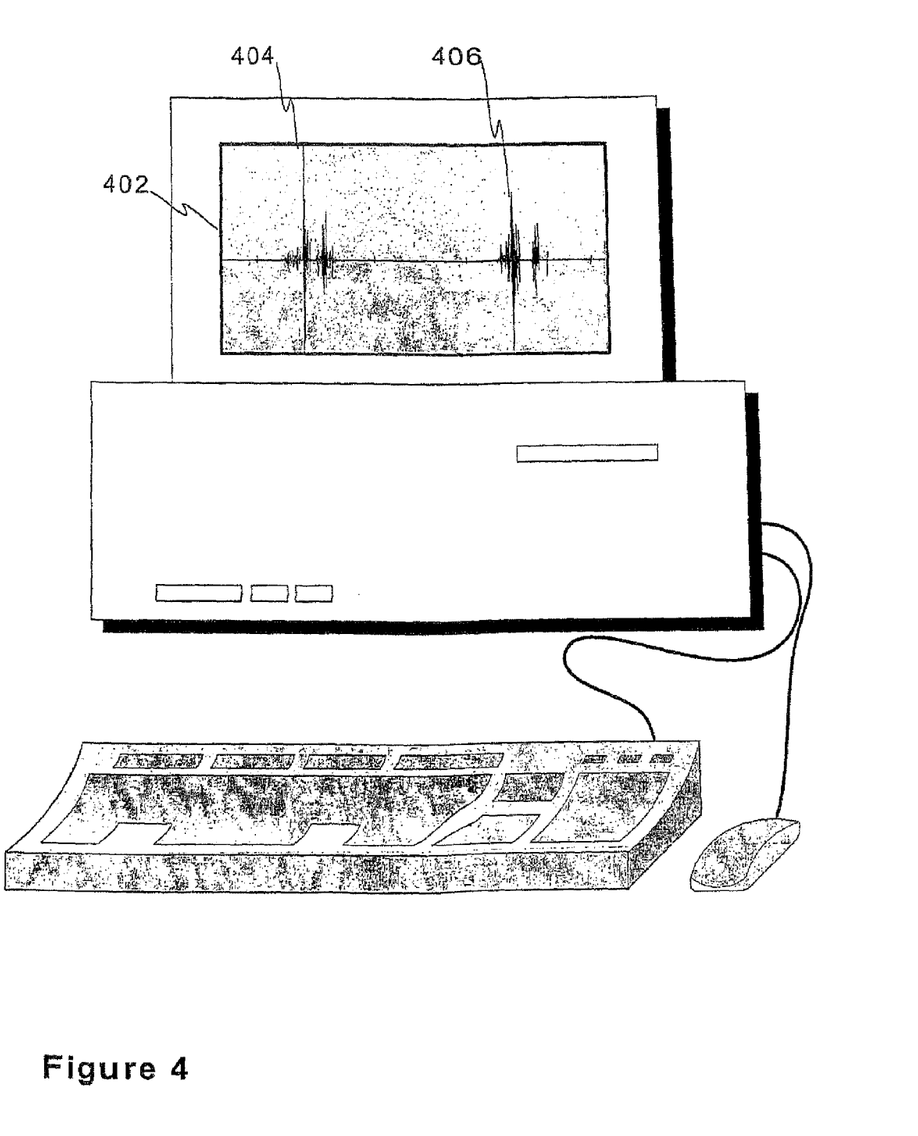
FIG. 4 depicts the features of an embodiment of the analysis software used in association with the current invention.

FIG. 4 visualizes a display view 402 of the computer application used for analyzing the measurement results. Further display views are also presented in FIG. 1 as thumbnail versions.

The view contains an example of one possible result of the analysis produced by the computer application. In the shown graph the time dimension extends a time period of approximately 10 seconds and two movements 404, 406 of the feet are detectable with the duration of about one second each having a pause of about 4 seconds between. The movements can be detected on the basis of their shape and/or amplitude being different from the base line of the detection level (either the horizontal axis, e.g. 'zero' axis, itself or a horizontal level with vertical separation from the horizontal axis), which is considered to be the base level of the signal lacking sounds generated by feet movements. The base level can be adjusted on the basis of background noise, i.e. the horizontal detection level is adjusted to follow the average noise level either directly or with additional safety margin. Alternatively, the base level can be even dynamically adjusted according to predetermined criteria utilizing e.g. a noise estimate for the decision-making. If the background noise has already been cancelled from or attenuated in the input sound signal, or if the analysis software is configured to cancel/attenuate the noise, the detection level may be lowered from the initial one due to the reduced average noise level. Software-based detection level determination is advantageous compared to the fixed-level detection of the occurrences of seizure-type movements.

The user of the analysis software, who may act as an expert in the research unit or be the subject himself (provided that he is familiar with the software due to training or comprehensive instructions), may input more specific start and end time of the sleep period to the analysis software either on his own initiative or in response to a request by the software. In home environment the measurement data is first transmitted from the storage to the analysis PC, if necessary. The data that has been optionally packed for storage and/or transmission is decoded for analysis and visual inspection by the analysis software. Respectively, in the research unit the measurement data is first received from a remote party, e.g. the subject or an intermediary and processed for analysis. For example, the packed data may have been stored in 4-bit differential format instead of the original 8 or 16-bit accuracy in the recording apparatus. The data are therefore unpacked. Thereafter the analysis may be performed automatically without need for manual intervention. However, trained users such as the medical staff may obtain better results by manually guiding the analysis e.g. through parameter twiddling and optimization.

In the following, one feasible embodiment of the analysis software is described in more detail.

During the analysis, the signal is "compressed" by calculating the area of the signal for each 0.1 sec epoch or other preferred period. This results in the compression of the data with a factor of 800 (when sampling rate=8 kHz).

Next, the median value for the epochs is calculated. This can be used as the noise level of the recording or the basic level of a continuous regular movement pattern. The triggering levels to detect the events like movements or snoring sounds may be calculated using the median level of the background noise as the base level of the signal. The software may be configured to detect a significant event, if the value exceeds three or four times the median level, or in connection with lack, pause or irregularity in the continuous movement pattern (e.g. apnea in respiratory movement recording), for example. Also other conditions in addition to or instead of comparisons with the median value can be utilized for detecting the significant events.

The software plots an output graph with the time elapsed as X-axis and the amplitude of the integrated signal as Y-axis. The scale of the X-axis may be altered manually and an epoch with special interest may be visualized. An overnight graph (e.g. 9 consecutive epochs of 60 min, totally 540 min) can be used as a basic output format for the graph.

The user may adjust the Y-axis and the detection level to determine significant signals/events. In automatic analysis the detection level can be adjusted using the median level of the background noise, for example.

Concerning the analysis of the movements, the movement events exceeding the detection level are analyzed. The number, duration, overall duration and statistical distributions of the movements are calculated. The periodic movement pattern can be identified using a special algorithm to find regularly repetitive movements with more than four occurrences, for example. The duration with periodic movements is calculated. The statistical analysis of the number and duration of the movements and of the periodic movements is performed. The movement patterns are indicated in a computer display unit using different colour codes.

As to the analysis of snoring, the significant snoring sound is detected when the area value of e.g. 0.1 sec epoch exceeds the detection level calculated from the median background noise level. A second of sound comprising signal exceeding the detection level is deemed as a snoring second. The snoring minute is correspondingly detected if more than 10 snoring seconds fall within one minute of the recording.

A heavy snoring is found when the level of the sound exceeds another, higher detection level. The artefact is found when the sound level is very high and not caused by snoring but by some other activity like talking, moving etc. The different detection (event) types (snoring, heavy snoring, artefact) can be indicated using different output colors in the graphs. For example, periodic occurrences of pauses or irregularities in the respiratory movement recording indicate apneas and are thus marked with certain color in the output graph.

The statistical analysis of the snoring includes duration, absolute and relative amounts and percentages of the different sound types (snoring, heavy snoring, artefact sounds) during the night.

The periodic snoring and periodic pauses in sound signal are indicating possible apneas. The sound signal is processed using a low-pass and a median filter. This eliminates isolated snoring sounds. The periodic occurrences of the snoring with periodic pauses are indicated via a colour code in the output and the duration of periodic breathing is also calculated and given.

The epochs of interest may be played back and listened. The user may indicate the time period of interest by defining a location on the graph with a mouse ('point and click'). The signal is then advantageously processed and fed through the loudspeakers of the computer. Thus the user may be able to ascertain that there really were snoring as indicated in the graphs. The software may be configured so as to process and playback the signal 10 times faster than real time. This can be achieved by cutting away 90% of the signal in short epochs, for example. Thus the frequency content of the signal is not changed but the playback time is shorter, which may quicken the auditive monitoring and tracking.

A hard copy of the analysis results may be printed including the graphic output and statistical analysis. The statistical parameters can be used to evaluate the possible abnormality of the recording, for example.

The software of the invention comprising the necessary program code, either for the recording/storage/forwarding devices (in case additional software is required for data capture, storage and transmission therein) or for the analysis device, or for both, can be provided as a computer program product on a carrier such as a CD-ROM, a DVD, a memory card/stick, a floppy disc, or other applicable medium. It may also be offered as a downloadable content.

The scope of the invention can be found in the following claims. Although the applicability of the invention was mainly described in the context of human subjects, the arrangement is applicable to animals as well provided that human management and assistance is given to properly position the equipment, initiate and stop the recording (if not remotely controlled/automatized), etc.

The invention claimed is:

1. A portable electronic arrangement for conducting sound-based measurements of sleep disorders, wherein a subject of the measurements is either a human or an animal, said arrangement comprising at least one microphone for capturing a sound signal, a processing unit for processing instructions, a memory for storing instructions and data, an attaching means for facilitating physical positioning to a predetermined measurement location of at least a chest or a limb of the subject or a nearby object, and a user input means for receiving control information,     wherein said arrangement is configured to initiate continuous, digital sound recording utilizing said at least one microphone in response to obtained control information to capture ambient sounds emanating from a vicinity of the measurement location during a measurement period and comprising sounds associated with movements of the subject, wherein said arrangement is configured to capture sounds of body movement against a contact surface external to the body, wherein the body movement is at least one element selected from a group consisting of: respiratory movement, body movement, tissue movement and limb movement, against the external contact surface, configured to store at least part of the recorded sound data in said memory, configured to stop the recording, upon termination of the measurement period, in response to an expiry of a timer or receipt of control information, wherein said arrangement further comprises sound-modifying material to be positioned on a sound path of the sound of the body movement against the contact surface external to the body to intentionally alter a spectral content of the sound associated with the body movement against the contact surface external to the body to fall on a preferred range relative to an apparatus according to a predetermined criterion prior to receipt by the microphone of the apparatus, wherein the material is configured to generate higher frequencies to the sound associated with the movement, and wherein the sound-modifying material alters the spectral content according to the predetermined criterion prior to receipt by the microphone, and wherein said microphone or at least part of an electronic consumer apparatus is coated with said sound-modifying material.

2. The arrangement of claim 1, comprising at least one portable electronic consumer apparatus including said microphone, said processing unit, said memory, and said user input means, and said apparatus further includes a communication means for transmitting sound data to a remote entity, wherein said control information is obtained via said communication means.

3. The arrangement of claim 1, wherein said attaching means includes at least one element selected from the group consisting of: a strap, a hook, a clip, a clasp, an indent, a projection, tape, an adhesive surface, an elastic band, a pocket, a stand, a mount, and a recess.

4. The arrangement of claim 1, comprising textile material including a garment or a blanket comprising said attaching means.

5. The arrangement of claim 1, comprising textile material including a garment comprising said attaching means and wherein said garment comprises at least one element selected from the group consisting of: a shirt, a vest, a sock, trousers, a glove, and a wristband.

6. The arrangement of claim 1, wherein the sound-modifying material comprises an object coated with, comprising a layer of, or being made of said sound-modifying material.

7. The arrangement of claim 1,
    wherein the sound-modifying material comprises an object coated with, comprising a layer of, or being made of said sound-modifying material, and
    wherein said object is an element selected from the group consisting of: a blanket, a sock, trousers, a vest, a shirt, a belt, and a pillowslip.

8. A portable electronic arrangement for conducting sound-based measurements of sleep disorders, wherein a subject of the measurements is either a human or an animal, said arrangement comprising at least one microphone for capturing a sound signal, a processing unit for processing instructions, a memory for storing instructions and data, an attaching means for facilitating physical positioning to a predetermined measurement location of at least a chest or a limb of the subject or a nearby object, and a user input means for receiving control information,     wherein said arrangement is configured to initiate continuous, digital sound recording utilizing said at least one microphone in response to obtained control information to capture ambient sounds emanating from a vicinity of the measurement location during a measurement period and comprising sounds associated with movements of the subject, wherein said arrangement is configured to capture sounds of body movement against a contact surface external to the body, wherein the body movement is at least one element selected from a group consisting of: respiratory movement, body movement, tissue movement and limb movement, against the external contact surface, configured to store at least part of the recorded sound data in said memory, configured to stop the recording, upon termination of the measurement period, in response to an expiry of a timer or receipt of control information, wherein said arrangement further comprises sound-modifying material to be positioned on a sound path of the sound of the body movement against the contact surface external to the body to intentionally alter a spectral content of the sound associated with the body movement against the contact surface external to the body to fall on a preferred range relative to an apparatus according to a predetermined criterion prior to receipt by the microphone of the apparatus, wherein the material is configured to generate higher frequencies to the sound associated with the movement, and wherein the sound-modifying material comprises an object coated with, comprising a layer of, or being made of said sound-modifying material, said object comprising a metal wire figure.

9. The arrangement of claim 1, further configured to process the captured sound signal and render at least part thereof for visualization, or further comprising a computer for storing the captured sound signal and for transferring it over a communications network to a remote system for analysis.

10. The arrangement of claim 1, further comprising a vest adapted to accommodate a sound recording apparatus and comprising a number of layers configured to elastically adapt to the respiratory movements of the subject.

11. The arrangement of claim 1, comprising a remote server configured to analyze the sound signal for sleep disorders.

12. The arrangement of claim 1, comprising at least one portable electronic consumer apparatus including said microphone, said processing unit, said memory, and said user input means, wherein at least part of said user input means is positioned in the apparatus to reduce a risk of accidental activation thereof.

13. The arrangement of claim 1, wherein the microphone is connected to an MP3 device with recording capability.

14. A portable electronic arrangement for conducting sound-based measurements of sleep disorders, wherein a subject of the measurements is either a human or an animal, said arrangement comprising at least one microphone for capturing a sound signal, a processing unit for processing instructions, a memory for storing instructions and data, an attaching means for facilitating physical positioning to a predetermined measurement location of at least a chest or a limb of the subject or a nearby object, and a user input means for receiving control information, wherein said arrangement is configured to initiate continuous, digital sound recording utilizing said at least one microphone in response to obtained control information to capture ambient sounds emanating from a vicinity of the measurement location during a measurement period and comprising sounds associated with movements of the subject, wherein said arrangement is configured to capture sounds of body movement against a contact surface external to the body, wherein the body movement is at least one element selected from a group consisting of: respiratory movement, body movement, tissue movement and limb movement, against the external contact surface, configured to store at least part of the recorded sound data in said memory, configured to stop the recording, upon termination of the measurement period, in response to an expiry of a timer or receipt of control information, wherein said arrangement further comprises sound-modifying material to be positioned on a sound path of the sound of the body movement against the contact surface external to the body to intentionally alter a spectral content of the sound associated with the body movement against the contact surface external to the body to fall on a preferred range relative to an apparatus according to a predetermined criterion prior to receipt by the microphone of the apparatus, wherein the material is configured to generate higher frequencies to the sound associated with the movement, and wherein the sound-modifying material is in a form of a rivet coated with, comprising a layer of, or being made of said sound-modifying material.

15. A portable electronic arrangement for conducting sound-based measurements of sleep disorders, wherein a subject of the measurements is either a human or an animal, said arrangement comprising at least one microphone for capturing a sound signal, a processing unit for processing instructions, a memory for storing instructions and data, an attaching means for facilitating physical positioning to a predetermined measurement location of at least a chest or a limb of the subject or a nearby object, and a user input means for receiving control information, wherein said arrangement is configured to initiate continuous, digital sound recording utilizing said at least one microphone in response to obtained control information to capture ambient sounds emanating from a vicinity of the measurement location during a measurement period and comprising sounds associated with movements of the subject, wherein said arrangement is configured to capture sounds of body movement against a contact surface external to the body, wherein the body movement is at least one element selected from a group consisting of: respiratory movement, body movement, tissue movement and limb movement, against the external contact surface, configured to store at least part of the recorded sound data in said memory, configured to stop the recording, upon termination of the measurement period, in response to an expiry of a timer or receipt of control information, wherein said arrangement further comprises sound-modifying material to be positioned on a sound path of the sound of the body movement against the contact surface external to the body to intentionally alter a spectral content of the sound associated with the body movement against the contact surface external to the body to fall on a preferred range relative to an apparatus according to a predetermined criterion prior to receipt by the microphone of the apparatus, wherein the material is configured to generate higher frequencies to the sound associated with the movement, and wherein the sound-modifying material is in a form of a plastic pearl coated with, comprising a layer of, or being made of said sound-modifying material.

16. The arrangement of claim 1, wherein the sound-modifying material is in a form of a blanket coated with, comprising a layer of, or being made of said sound-modifying material.

* * * * *

UNITED STATES PATENT AND TRADEMARK OFFICE
CERTIFICATE OF CORRECTION

PATENT NO. : 8,540,650 B2  Page 1 of 1
APPLICATION NO. : 12/158075
DATED : September 24, 2013
INVENTOR(S) : Salmi et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 915 days.

Signed and Sealed this

Fifteenth Day of September, 2015

Michelle K. Lee
*Director of the United States Patent and Trademark Office*